United States Patent [19]

Lottick

[11] Patent Number: 4,552,143
[45] Date of Patent: Nov. 12, 1985

[54] REMOVABLE SWITCH ELECTROCAUTERY INSTRUMENTS

[76] Inventor: Edward A. Lottick, 789 Wyoming Ave., Kingston, Pa. 18704

[21] Appl. No.: 443,517

[22] Filed: Nov. 22, 1982

Related U.S. Application Data

[63] Continuation-in-part of Ser. No. 242,746, Mar. 11, 1981, Pat. No. 4,370,980.

[51] Int. Cl.⁴ .............................................. A61B 17/39
[52] U.S. Cl. ..................... 128/303.14; 128/303.17; 200/157; 200/281; 200/282; 200/295
[58] Field of Search ...................... 128/303.13–303.19, 128/800, 801; 219/240; 200/157, 281, 282, 295, 338

[56] References Cited

U.S. PATENT DOCUMENTS

| | | | |
|---|---|---|---|
| 1,071,978 | 9/1913 | White | 128/303.13 |
| 2,176,479 | 10/1939 | Willis | 128/303.13 |
| 3,100,489 | 8/1963 | Bagley | 128/303.17 |
| 3,752,160 | 8/1973 | Billin | 128/303.17 |
| 3,878,348 | 4/1975 | German | 200/157 |
| 3,911,241 | 10/1975 | Jarrard | 128/303.17 X |
| 4,032,738 | 6/1977 | Esty et al. | 128/303.13 X |
| 4,034,761 | 7/1977 | Prater et al. | 128/303.14 |

FOREIGN PATENT DOCUMENTS

| | | | |
|---|---|---|---|
| 757933 | 1/1934 | France | 128/303.14 |
| 575103 | 10/1977 | U.S.S.R. | 128/303.14 |

OTHER PUBLICATIONS

Stevenson, "Combined Diathermy Forceps & Scissors", The Lancet, Oct. 24, 1959, pp. 650-651.

*Primary Examiner*—Lee S. Cohen
*Attorney, Agent, or Firm*—Michael F. Petock

[57] ABSTRACT

A family of removable switch electrocautery instruments is provided by springably releasably mounting a switch means to an instrument provided with a conductive member adapted to come into contact with living tissue and a handle member. The handle member may be formed of conductive material covered with an insulative layer or the handle member may be comprised of an insulative material. Means are provided on the switch means for making an electrical connection with the conductive member which was adapted to come into contact with the living tissue. Electrical connection between the switch means may be made through one of the springably releasable attachments or it may be made by means of a separate connector element.

23 Claims, 15 Drawing Figures

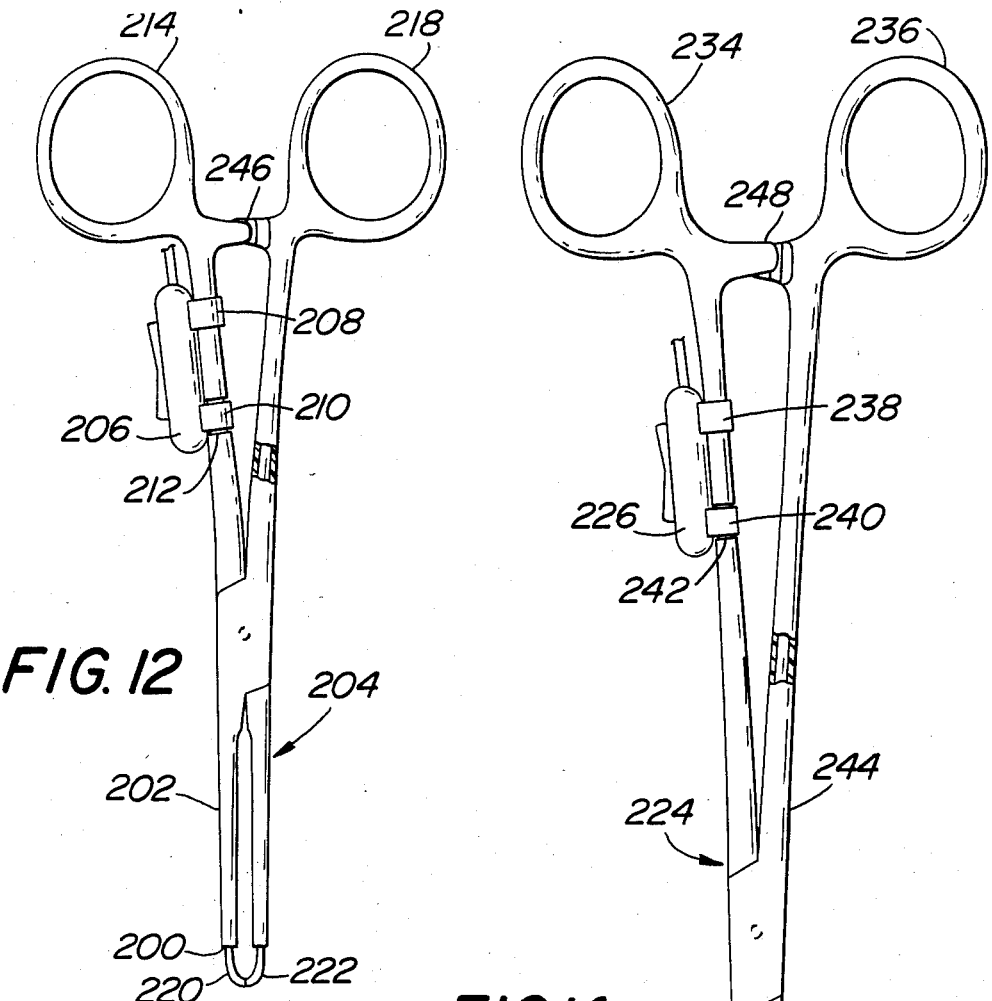

REMOVABLE SWITCH ELECTROCAUTERY INSTRUMENTS

CROSS-REFERENCE TO RELATED APPLICATION

This application is a continuation in part application of U.S. patent application Ser. No. 242,746, filed Mar. 11, 1981 by the inventor herein, and which is entitled "ELECTROCAUTERY HEMOSTAT" now U.S. Pat. No. 4,370,980.

BACKGROUND OF THE INVENTION

The present invention relates to a family of electrocautery instruments provided with a removable switch.

Electrocautery has become widely used in surgery today. Electrocautery is utilized to provide hemostasis or control of bleeding during surgery, for cutting, and the burning or disintegration of diseased tissue, such as malignant, premalignant tissue or dysplastic tissue.

Electrocautery instruments are known in the prior art. For example, reference may be had to U.S. Pat. Nos. 3,100,489; 3,643,663; 4,005,714; 4,076,028 and 4,041,952.

However, several significant disadvantages remain with electrocautery instruments heretofore in use. For example, instruments utilized in surgery must be made aseptic. This requires the placing of instruments in an autoclave for a significant period of time under adverse conditions of heat, pressure and steam. It is difficult, if not impossible, for electrical components to withstand such conditions on repeated use. Therefore, attempts have been made to produce instruments which are disposable, that is may be utilized and disposed of. However, this is relatively expensive.

Furthermore, the instruments are typically connected irremovably to the electrical cable which connects the instrument to the supply of electrical energy. Therefore, there is a lack of versatility in being able to connect various instruments, easily and efficiently, to the supply of electrical energy for rapid use on the surgical field unless a multitude of cables are run to the surgical field. However, it is undesirable to have more items than necessary on the surgical field, and particularly undesirable to have three, four or five cables with various instruments connected thereto.

Furthermore, during the use of an electrocautery instrument, crusting or burnt material accumulates on the electrocautery tip. This, heretofore, necessitated the scraping or other cleaning of the electrocautery tip or the replacement of the electrocautery instrument, including the reconnection of another cable to the source of electrical energy. In either case, this required a certain amount of time which adds further to the length of time that the patient is under general anesthesia, which is in general undesirable.

SUMMARY OF THE INVENTION

Briefly, in accordance with the present invention, a family of electrocautery instruments is provided in which a conductive member adapted to come into contact with living tissue is provided. A handle member is provided either formed on or connected to the conductive member. The handle member may be comprised of an insulated material or, if formed from the same conductive material as the conductive member adapted to come into contact with the living tissue, may be provided with an insulative covering. In either case, either the insulated handle or the insulative covering is provided with an opening therethrough for enabling an electrical connection to the conductive member. Switch means is provided which is releasably attachable to the handle member. The switch means is provided with at least one releasable connection to the conductive member and means for connecting to a source of electrical energy whereby the switching means may be readily removed and replaced on the electrocautery instrument.

The releasable switch means may preferably be springably releasably attached to the handle member.

It is an important aspect of the present invention to provide a switch means which requires a minimun of force for the operation thereof to prevent inadvertent moving of the electrocautery instrument by the surgeon when power is applied to the electrocautery instrument.

The releasably attachable switch means in accordance with the present invention may be provided for use in connection with a large family of electrocautery surgical instruments, including probes, pens, wands, knobs, scapels and various types of grasping or clamping devices including those known as mosquito clamps, hemostats, tonsil hemostats, right angles, Allis clamps, Babcock clamps and forceps or tweezers. The releasable attachable switch means may be provided in connection with various sizes of these instruments.

An advantage of the present invention is that the switching mechanism may be readily separated from the electrocautery instrument such as the scapel or wand, hemostat, tweezers or the like. This provides a number of significant advantages. This means that various ones of the surgical instruments may be connected to the source of electrical energy at will by the surgeon on the surgical field without interruption of the surgery. Furthermore, the expensive surgical instrument, such as the hemostat, Allis or Babcock clamp may be readily autoclaved and a new switch snapped on after the autoclaving. Furthermore, if a bleeding blood vessel is clamped by an electrocautery hemostat in accordance with the present invention, and it is desired to leave the hemostat in place for a period of time during the surgery, the electrical switch means may be readily removed from the hemostat and applied to another instrument.

Furthermore, if an electrocautery instrument tip became crusted with burnt debris, a new instrument may be readily connected to the electrical source by removing the releasable switch from the crusted instrument and snapping it onto a new instrument. It is much more time efficient to perform this procedure than to try to scrape the tip of the electrocautery instrument clean during the surgery. This is also more time efficient than the complete connection of a new electrical instrument to the supply of electrical energy. The crusted electrical instruments may be scraped and scrubbed after the surgery, thereby avoiding any lengthening of the period of time under which the surgical patient is under general anesthesia.

BRIEF DESCRIPTION OF THE DRAWINGS

For the purpose of illustrating the invention, there are shown in the drawings forms which are presently preferred; it being understood, however, that this invention is not limited to the precise arrangements and instrumentalities shown.

FIG. 12 is an elevation view of an electrocautery Allis clamp having a removable switch in accordance with the present invention.

FIG. 13 is an elevation view of an electrocautery Babcock clamp having a removable switch in accordance with the present invention.

FIG. 14 is a cross-sectional view of an electrocautery pen having an insulative handle with an electrical contact mounted therein for use in conjunction with a removable switch in accordance with the present invention.

FIG. 15 is a broken away cross-sectional view of a handle of an electrocautery instrument having an electrical ring contact mounted on the outside thereof.

DETAILED DESCRIPTION OF THE PREFERRED EMBODIMENTS

Figure 1:
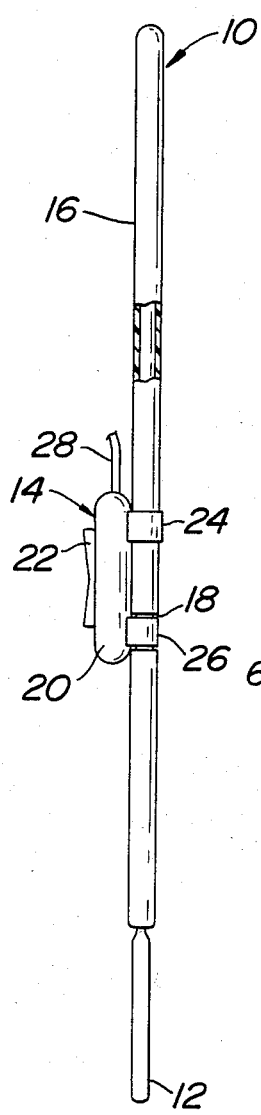
FIG. 1 is an elevation view of an electrocautery scapel having a removable electrical switch in accordance with the present invention.

Referring now to the drawings, wherein like numerals indicate like elements, there is shown in FIG. 1 one of a family of electrocautery instruments which comprise the present invention. There is shown in FIG. 1 a scapel or scapel-like instrument 10. The scapel or scapel-like instrument 10 is provided with a conductive member 12 which is adapted to come into contact with living tissue. The exposed end of conductive member 12 serves as the cutting or cauterization element in response to the application of one of two predetermined potentials to conductive member 12 via switch 14. Scapel-like instrument 10 is provided with a handle 16 which may be comprised of an insulating or non-conductive material or the handle may be comprised of conductive material formed as an extension of conductive member 12 and coated with an insulating material such as latex or other synthetic material. It is important that some form of insulation be provided between conductive member 12 and the surgeons hand. In either case, an opening 18 is provided to enable an electrical connection to an extension of conductive member 12 running within handle 16.

Switch 14 is provided with a housing 20 and manually operable member 22. Switch housing 20 is provided with clamping members 24 and 26. Clamping members 24 and 26 are preferably springably releasable members which are readily clamped onto the instrument 10 and readily removed from the instrument 10. Clamping members 24 and 26 may be made of any suitable resilient material, such as spring steel or brass of suitable dimensions. One of the clamping members may be electrically connected to a source of electricity through the mechanism of switch 14 and as shown in FIG. 1, clamping member 26 is electrically connected to a source of electrical energy through the mechanism of switch 14. The opening 18 in handle 16 enables the connection of electricity to conductive member 12. Since electrical current is applied through clamping member 26 during the cutting or cauterization procedures, the outer surface of clamp 26 may be provided with an insulative covering, such as a layer of latex. Electrical energy is supplied to switch 14 via cable 28.

Figure 2:
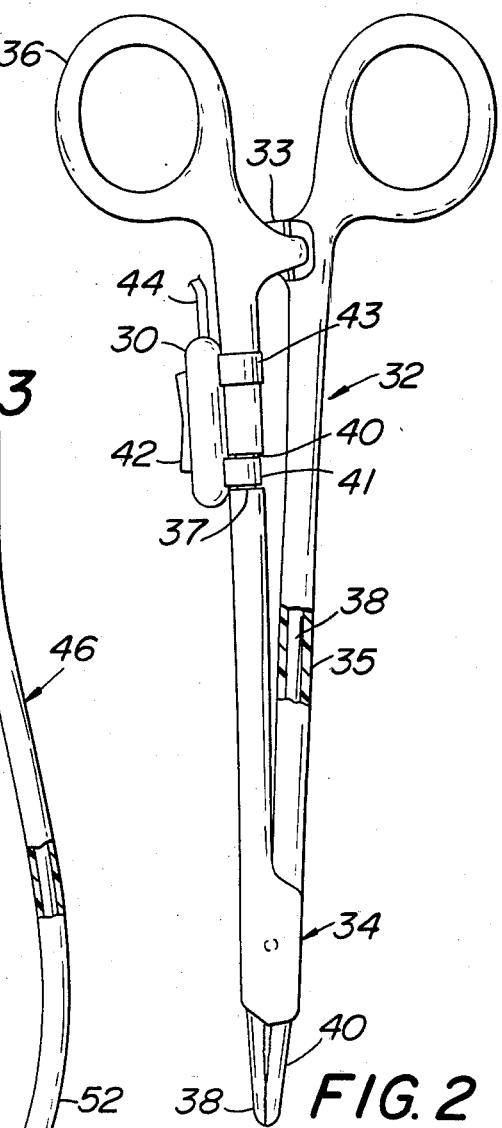
FIG. 2 is an elevation view of an electrocautery hemostat having a removable switch in accordance with the present invention.

Referring now to FIG. 2, there is shown an electrical switch 30 applied to an electrocautery hemostat 32 in a manner similar to that shown and described in applicant's co-pending application Ser. No. 242,746 referred to above. Switch 30 is preferably releasably retained on hemostat 32 by clamps 41 and 43. The hemostat shown in FIG. 2 is provided with an insulative covering 35 extending at least from the pivot point 34 to the handle end of the hemostat 36 with the exception of an opening 37 for clamp 41 for application of an electrical connection to the conductive member 40. A portion of conductive members 38 and 40 is adapted to come into contact with living tissue for the application of electrocauterization or cutting depending upon the position of manually operable member 42 of switch 30. Power is applied to switch 30 via cable 44. The hemostat 32 is provided with locking means for locking the jaws 38 and 40 in an engaged position.

Figure 3:
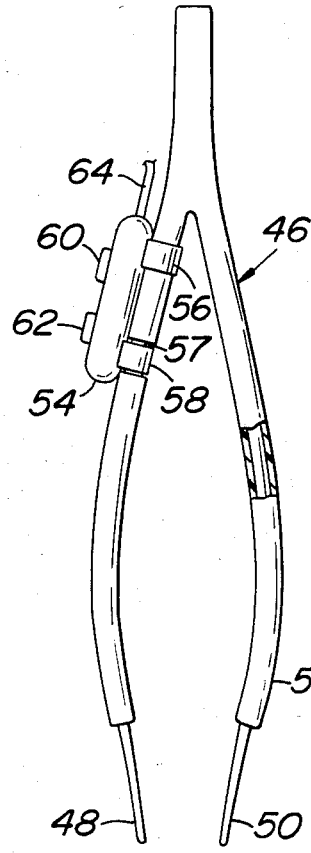
FIG. 3 is an elevation view of an electrocautery tweezer or forceps having a removable switch in accordance with the present invention.

Referring now to FIG. 3, there is shown a tweezer or forceps 46 to which an electrocautery switch may be applied in accordance with the present invention. The tweezers or forceps 46 are comprised of a suitable conductive material comprised of conductive members 48 and 50. Members 48 and 50 are provided with a suitable insulative covering such as latex at 52. Switch 54 is springably releasably attached to tweezer member 48 via clamps 56 and 58. An opening 57 is provided in insulative covering 52 for the making of an electrical connection via clamp 58 to electrically conductive member 48. Electrically conductive member 48 is adapted to come into contact with living tissue and, upon the application of an electrical current to conductive member 48 via switch 54, a cauterization or electrocautery cutting is performed depending upon which one of two operable switches 60 or 62 is depressed. The electrical energy is applied to switch 54 via cable 64.

Electrical switches 14, 30 and 54 may be releasably attached to the surgical instruments by means other than those described herein. However, preferably, the electrical switches are readily attachable and disattachable in a preferred manner by a springably releasable clamping means which may be readily clamped onto and removed from surgical instruments during the performance of an operation without delay.

Figure 4:
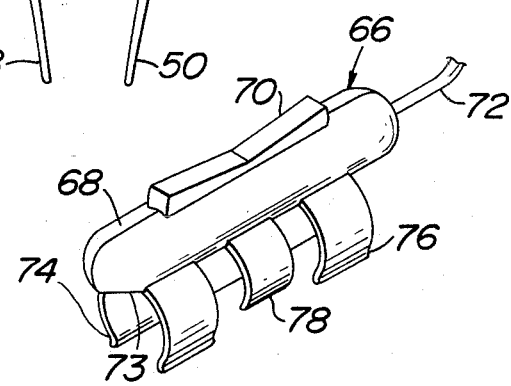
FIG. 4 is a view in perspective of an alternate embodiment of a switch means in accordance with the present invention.

Referring to FIG. 4, there is shown an alternate embodiment of a switch 66 which may be utilized in accordance with the present invention. Switch 66 is provided with a housing 68, a manually operable switching member 70 and a cable 72 for the application of electrical energy. Switch 66 is provided with clamps 74 and 76 for securing the switch 66 to a surgical instrument. A separate clamping member 78 is provided for the application of electrical energy to the conductive element of the surgical instrument. The clamps 74, 76 and 78 are attached to the flat undersurface 73 of switch housing 68.

Figure 5:
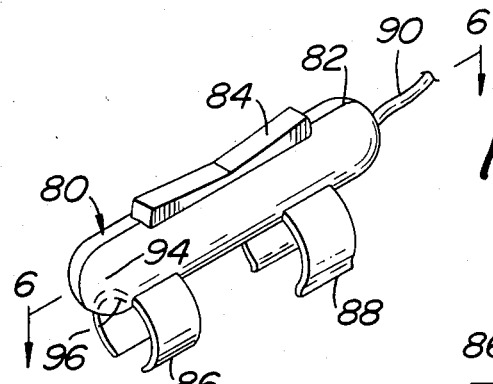
FIG. 5 is a view in perspective of an alternate embodiment of an electrocautery switch in accordance with the present invention.

Referring now to FIG. 5, there is shown another embodiment of a switch 80 which may be utilized in accordance with the present invention. Switch 80 is provided with a housing 82 and a manually operable member 84. Housing 82 is provided with resilient members 86 and 88. An electrical cable 90 is provided to supply electrical energy. Housing 82 is specially formed to provide a minimum amount of bulk on the surgical instrument and is formed in an oval or rounded shape as shown at 94 to provide increased comfort and ease of use by the surgeon. The clamping members 86 and 88 are formed into or recessed into housing 82 as shown at 96 to reduce to a minimum the amount of bulk or heighth of the housing on top of the surgical instrument.

Figure 6:
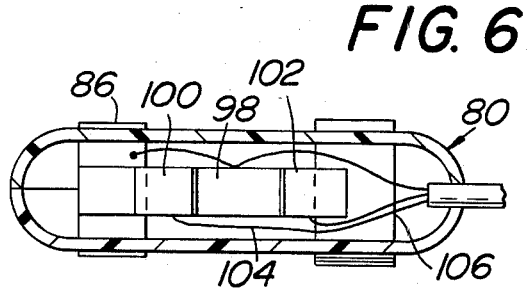
FIG. 6 is a cross-sectional view taken along line 6—6 of FIG. 5.

Referring to FIG. 6, there is shown a plan view of one embodiment of the electrical connections within switch 80. Electrically conductive clamp 86 is shown electrically connected to electrically conductive switch element 98. Electrical energy of one potential is applied to electrical switch conductive member 100 via wire 104 and an electrical potential of a second value is applied to electrical switch conductor member 102 via wire 106. For example, the potential applied to conductive element 100 may be utilized for cauterization and potential applied to element 102 may be of a greater value utilized in cutting tissue. The operation of manually operable switch member 84 makes an electrical connection between conductive element 98 and either conductive element 100 or 102 to apply the desired electrical potential to electrically conductive clamping member 86 for the application of the desired voltage to the end of the surgical instrument which is to be placed in contact with the living tissue.

Figure 8:
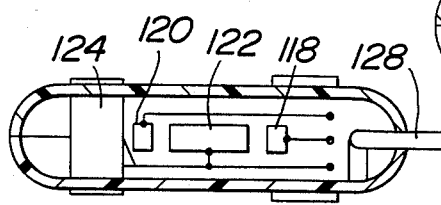
FIG. 8 is a plan view of the electrical contacts of the electrocautery switch shown in FIG. 7.
Figure 7:
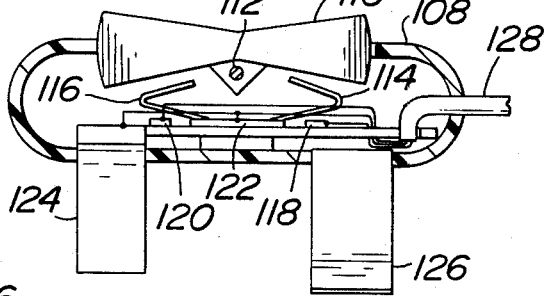
FIG. 7 is a cross-sectional elevation view of an alternate embodiment of an electrocautery switch arrangement in accordance with the present invention.

Referring now to FIGS. 7 and 8, there is shown an alternate embodiment of a switch in accordance with the present invention. There is shown a housing 108 and a manually operable switch member 110. Manually operable switch member 110 is pivotable at point 112 to operate either spring element 114 or 116. If manually operable switch member 110 is depressed on the left, spring 116 is pressed into contact with electrical contact 120 making an electrical connection between electrical contact 120 and printed circuit board contact 122. The printed circuit board contact 122 is in electrical contact with clamp 124 which makes the electrical connection to the conductive element of the electrocautery instrument which is adapted to come into contact with the living tissue. Clamping member 126 may be utilized to merely help retain switch housing 108 in position on the surgical instrument. The electrical energy is applied to the switch via cable 128.

Figure 9:
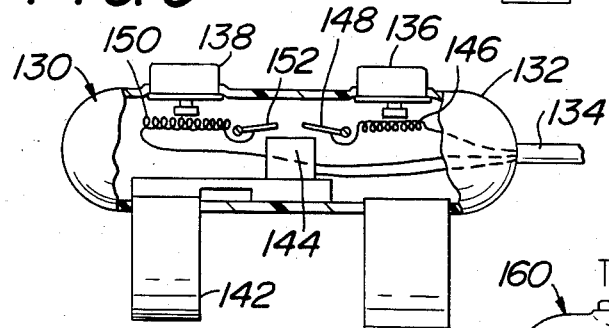
FIG. 9 is a schematic diagram of an alternate electrocautery switch arrangement which may be utilized in accordance with the present invention.

Referring now to FIG. 9, there is shown a schematic diagram of another embodiment of a suitable switch which may be utilized in accordance with the present invention. In accordance with the embodiment shown in FIG. 9, an easy to operate switch 130 is shown with a housing 132. Electrical energy is supplied via cable 134 and a pair of manually operable switch means are provided at 136 and 138. For example, the depression of the switch member 136 may be utilized for cutting, and the depression of the switch member 138 may be used for cauterization procedures. The switch housing 132 is attached to the electrocautery surgical instrument by means of clamps 140 and 142. Clamp 142 also serves the function of electrical conduction of electrical energy via the switch mechanism to the conductive member of the electrocautery instrument which is adapted to come in contact with the living tissue. Clamping member 142 is connected to switch contact 144. The desired potential is applied to contact 144 by either the depression of manually operable switch member 136 which causes a stretching of spring 146 and the closing of switch member 148 onto contact 144, or the depression of manually operable switch member 138 which causes the elongation of spring member 150, which causes the closing of switch member 152 onto contact 144. The utilization of spring members as shown provides an easy to operate switch.

Figure 10:
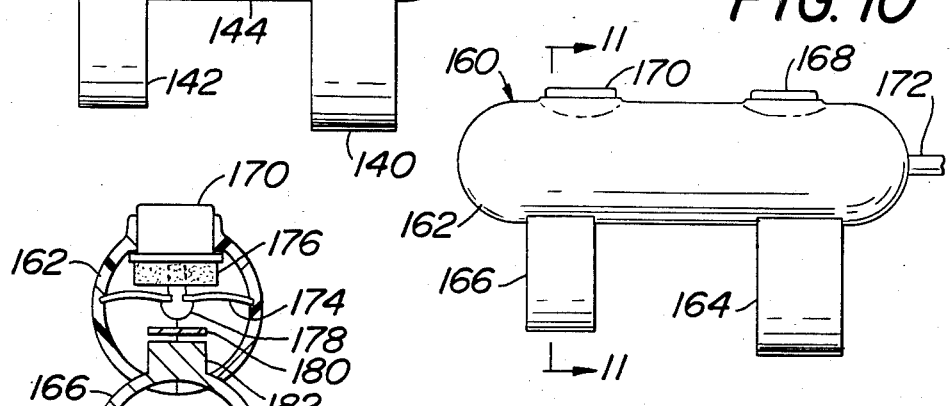
FIG. 10 is an elevation view of an alternate embodiment of an electrocautery switch in accordance with the present invention.
Figure 11:
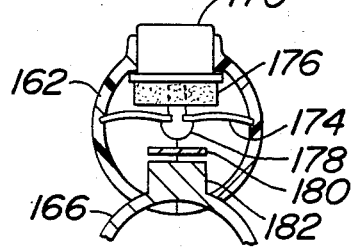
FIG. 11 is a cross-sectional view taken along line 11—11 of FIG. 10.

Referring now to FIGS. 10 and 11, there is shown another embodiment of a switch in accordance with the present invention. There is shown a switch 160 which is of the easy to operate type. Switch 160 is provided with a housing 162 and clamping members 164 and 166. Switch 160 is provided with a pair of depressable manually operated switch members 168 and 170. Electrical current is applied to the switch through cable 172.

Referring now to FIG. 11, there is shown a cross-sectional view taken along line 11—11 of FIG. 10. Depressable member 170 is mounted within plastic housing 162 by means of a flexible steel spring 174. A sponge rubber cushion is provided under manually depressable member 170 and around plunger 178 of manually depressable member 170. Plunger 178 depresses contact element 180 onto contact element 182 to apply a selected electrical potential to electrically conductive clamping member 166. A combination of the structure and spring element 174, in conjunction with sponge cushion 176, provides an easy to operate electrical switch which is important in surgical operations. The switch utilized on the surgical instruments should operate with a minimum of pressing by the surgeon to avoid movement of the surgical instrument during the turning on or off of the switch.

Referring now to FIG. 12, there is shown an electrocautery instrument in the form of an Allis clamp having a removable electrical switch in accordance with the present invention. There is shown in FIG. 12 a conductive member 200 in the form of an Allis clamp. Conductive member 200 is provided with an insulative covering 202, which may preferably be latex. Electrocautery instrument 204 as shown in FIG. 12 is provided with a removable switch 206, which may be similar to any one of the various embodiments of the switch heretofore described. Switch 206 is provided with a mechanical clamp 208 and a second clamp 210 which provides the combined functions of mechanically attaching the switch 206 to the instrument and the function of providing an electrical connection via opening 212 in insulative covering 202. The Allis clamp 204 is provided with handles 214 and 218, which are provided with the insulative covering 202, and conductive offset mating jaws 220 and 222 which are provided with mating teeth.

Referring now to FIG. 13, there is shown an electrocautery instrument 224 in the form of a Babcock clamp which is provided with a removable electrical switch 226 in accordance with the present invention. The Babcock clamp 224 is comprised of an electrically conductive material 228 which forms a pair of mating jaws 230 and 232 with concave surfaces. The conductive material may extend through the Babcock clamp and form the handles 234 and 236. Alternatively, in this instrument, and in the other instruments described herein, the handles may be formed of an insulative or nonconducting material, with the conductive jaws, or other portion of the instrument which is intended to come into contact with the tissue to be electrocauterized, being provided with an electrical connection to the removable switch. The removable switch 226 is provided with clamps 238 and 240. Clamp 238 forms solely a mechanical clamping function whereas clamp 240 provides a dual function of mechanically clamping the switch 226 to the instrument and provides an electrical connection to conductive element 228 via an opening 242 through insulative covering 244. Both the Allis clamp of FIG. 12 and the Babcock clamp of FIG. 13 are provided with means similar to that of a hemostat, at 246 and 248 respectively, for locking the jaws in a preselected engaged position.

FIG. 14 is an alternate embodiment of the invention wherein an electrically conductive element 250 is mounted within an insulative handle, such as one comprised of one of the synthetic resins, without the conductive element extending through the handle. The structure shown in FIG. 14 is sometimes referred to in the surgical art as an electrocautery pen. The electrically conductive element 250 which is adapted to come into contact with living tissue for the purpose of cauterization is connected by means of a wire 254 to a ring or other suitable contact 256 mounted within handle 252. The openings 258 and 260 in handle 252 preferably do not go around the entire circumference of handle member 252. However, if it is desired to do so, ring element 256 may be adequately secured to the bifurcated portions of handle 252 to provide adequate structural rigidity. In use, a removable electrical switch could be snapped onto handle 252 with the smaller diameter electrical contacts snapping onto ring contact 256.

Other variations of this structure are within the scope of the present invention, including the mounting of a conductive ring on the outside surface of an insulative handle with the wire passing through the insulative handle to make contact with ring contact as illustrated in FIG. 15. FIG. 15 illustrates a portion of an insulative handle 262 having a ring or other suitable electrical contact 264 mounted on the surface thereof. An electrical connection is provided to electrically conductive element (not shown) adapted to come into contact with tissue for cauterization or cutting via wire 266. Other variations of the contact structure are within the scope of the present invention.

Various electrical switches as described herein may be applied to various surgical instruments including, but not limited to, probes, pens, wands, knobs and scapels of various sizes and kinds, and also may be applied to various types and sizes of grasping or clamping devices including mosquito hemostats, standard hemostats, Kelly hemostats, tonsil hemostats, right angle hemostats, Allis clamps, Babcock clamps and forceps and tweezers.

In accordance with the present invention, both clamping and electrical connections may be made through one of the two clamp members, which may preferably be stainless steel, spring clamps of appropriately thin dimensions. This type of a releasable attaching means enables connection and disconnection of the electrical switch with ease in a rapid manner adaptable for quick and easy changes during surgical operations. The rapid connection and disconnection of the switching mechanism also enables autoclaving of the more expensive portion of instruments, such as hemostats, Allises and Babcocks, and enables the switching mechanism to be readily replaced at will. Furthermore, the quick and easy attachment and disattachment of the electrical components enables ready substitution of the electrocautery function to various instruments as the need arises during the surgical procedure. For example, if the electrical switch is applied to a hemostat which is attached to a bleeding blood vessel, and the surgeon desires to leave that hemostat in place, perhaps on a major vessel, the electrical switch may be readily disconnected and applied to another hemostat or other surgical instruments with ease by the surgeon without the need for interface with parties not directly involved in the surgery.

In view of the above, the present invention may be embodied in other specific forms without departing from the spirit or essential attributes thereof and, accordingly, reference should be made to the appended claims, rather than to the foregoing specification as indicating the scope of the invention.

I claim:

1. An electrocautery instrument, comprising:
    a conductive member adapted to come into contact with tissue for electrocauterization;
    a handle on said conductive member enabling said conductive member to be positioned by surgical personnel;
    means for electrically insulating said conductive member from said surgical personnel, said electrical insulating means including enabling means for enabling an electrical connection to said conductive member; and
    switch means including at least one electrically conductive spring clamp member releasably attaching said switch means to said handle, said switch means having at least one releasable electrical connection to said conductive member via said spring clamp member and said enabling means, and said switch means including means for electrically connecting said spring clamp member to a source of electrical energy, whereby said switch means may be readily removed from and replaced on said electrocautery instrument.

2. An electrocautery instrument in accordance with claim 1 wherein said electrical insulating means comprises said handle member comprised of an insulating material.

3. An electrocautery instrument in accordance with claim 1 wherein said electrical insulating means comprises a layer of insulating material provided over an extension of said conductive member which forms of said handle.

4. An electrocautery instrument in accordance with claim 3 wherein said electrical insulating means is comprised of a layer of latex.

5. An electrocautery instrument in accordance with claim 1 wherein said switch means is provided with a second spring clamp member releasably attaching said switch means to said handle.

6. An electrocautery instrument in accordance with claim 5, wherein said electrically conductive spring clamp member is releasably attached to said conductive member and the other spring clamp member includes a pair of clamps releasably attached to said electrical insulating means.

7. An electrocautery instrument in accordance with claim 1 wherein said switch means is provided with a housing having a substantially oval cross-section.

8. An electrocautery instrument in accordance with claim 6 wherein said housing of said switch means is provided with a recess receiving said spring clamp member and a portion of said handle of said electrocautery instrument in order to reduce the bulk of the electrocautery instrument with said switch means applied thereto.

9. An electrocautery instrument in accordance with claim 1 wherein said electrically connecting means of said switch means is provided with electrical contact means for connecting one of two different electrical potentials to said conductive member.

10. An electrocautery instrument in accordance with claim 1 wherein said switch electrically connecting means of said means includes electrical contact means which includes a coil spring, an electrical contact connected to one end of said coil spring and a depressable member, said depressable member engaging said coil spring transversely, the transverse engagement of said coil spring causing a lengthening of the coil spring and the drawing of said electrical contact to an electrical energy transmitting condition between said enabling means and said source of electrical energy.

11. An electrocautery instrument in accordance with claim 1 wherein said electrical connecting means of said switch means includes electrical contact means which includes an electrical contact, a flexible spring steel member and a depressable member having a plunger attached thereto, said plunger being retained by said flexible spring steel member, a cushion being provided between said spring steel member and said depressable member, said plunger causing the closing of said electrical contact upon depression of the depressable member to an electrical energy transmitting condition between said enabling means and said source of electrical energy.

12. An electrocautery instrument in accordance with claim 1 wherein said switch means is provided with electrical contacts formed on a printed circuit board.

13. An electrocautery instrument in accordance with claim 1 wherein said conductive member forms a probe-like instrument.

14. An electrocautery instrument in accordance with claim 1 wherein said conductive member forms a scapel.

15. An electrocautery instrument in accordance with claim 1 wherein said conductive member forms a hemostat.

16. An electrocautery instrument in accordance with claim 1 wherein said conductive member forms an Allis clamp.

17. An electrocautery instrument in accordance with claim 1 wherein said conductive member forms a Babcock clamp.

18. An electrocautery instrument in accordance with claim 1 wherein said conductive member forms a tweezer.

19. An electrocautery instrument in accordance with claim 1 wherein said conductive member forms a surgical pen.

20. An electrocautery instrument in accordance with claim 1 wherein said enabling means includes a conductive contact to which said electrically conductive spring clamp member is releasably attached, said conductive contact being electrically connected to said conductive member.

21. An electrocautery instrument in accordance with claim 20, wherein said enabling means additionally includes a conductive wire within said handle and operably connected to both said conductive member and said contact.

22. An electrocautery instrument in accordance with claim 20, wherein said conductive contact comprises a contact mounted in said insulative handle.

23. An electrocautery instrument in accordance with claim 20, wherein said conductive contact comprises a contact mounted on said insulative handle.

* * * * *